(12) United States Patent
Wong

(10) Patent No.: US 11,637,378 B2
(45) Date of Patent: Apr. 25, 2023

(54) COILED DIPOLE ANTENNA

(71) Applicant: INTUITIVE SURGICAL OPERATIONS, INC., Sunnyvale, CA (US)

(72) Inventor: Serena H. Wong, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 708 days.

(21) Appl. No.: 16/670,847

(22) Filed: Oct. 31, 2019

(65) Prior Publication Data

US 2020/0138515 A1    May 7, 2020

Related U.S. Application Data

(60) Provisional application No. 62/844,328, filed on May 7, 2019, provisional application No. 62/754,886, filed on Nov. 2, 2018.

(51) Int. Cl.
| | |
|---|---|
| *H01Q 9/16* | (2006.01) |
| *H01Q 21/06* | (2006.01) |
| *H01Q 9/30* | (2006.01) |
| *H05B 6/72* | (2006.01) |
| *A61B 18/18* | (2006.01) |
| *A61B 18/00* | (2006.01) |

(52) U.S. Cl.
CPC ............ *H01Q 9/16* (2013.01); *H01Q 9/30* (2013.01); *H01Q 21/062* (2013.01); *H05B 6/72* (2013.01); *A61B 18/1815* (2013.01); *A61B 2018/00577* (2013.01); *A61B 2018/1838* (2013.01); *A61B 2018/1846* (2013.01)

(58) Field of Classification Search
None
See application file for complete search history.

(56) References Cited

U.S. PATENT DOCUMENTS

| | | | | |
|---|---|---|---|---|
| 6,016,130 | A | * | 1/2000 | Annamaa ............... H01Q 5/371 |
| | | | | 343/702 |
| 6,380,732 | B1 | | 4/2002 | Gilboa |
| 6,389,187 | B1 | | 5/2002 | Greenaway et al. |
| 7,416,681 | B2 | | 8/2008 | Kim et al. |
| 7,772,541 | B2 | | 8/2010 | Froggatt et al. |
| 8,900,131 | B2 | | 12/2014 | Chopra et al. |
| 9,259,274 | B2 | | 2/2016 | Prisco |
| 9,452,276 | B2 | | 9/2016 | Duindam et al. |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Shirley X Jian
(74) *Attorney, Agent, or Firm* — Haynes and Boone, LLP

(57) ABSTRACT

An antenna system comprises a transmission member and an antenna at a distal end of the transmission member. The antenna includes a first conductive arm, an insulator extending around the first conductive arm, and a second conductive arm wound around at least a first portion of the insulator to form a second conductive arm coil. A property of the insulator varies along an insulator longitudinal axis of the insulator. The insulator includes a set of formed patterns along at least a portion of the insulator longitudinal axis.

20 Claims, 10 Drawing Sheets

(56) References Cited

U.S. PATENT DOCUMENTS

| | | | |
|---|---|---|---|
| 11,280,863 B2* | 3/2022 | Wong | A61B 34/20 |
| 2003/0195499 A1* | 10/2003 | Prakash | A61B 17/29 |
| | | | 606/33 |
| 2006/0013523 A1 | 1/2006 | Childlers et al. | |
| 2008/0266203 A1* | 10/2008 | Rossetto | A61B 18/1815 |
| | | | 343/895 |
| 2011/0213351 A1* | 9/2011 | Lee | A61B 18/1815 |
| | | | 606/41 |
| 2015/0250540 A1 | 9/2015 | Behdad et al. | |
| 2018/0256251 A1 | 9/2018 | Hagness et al. | |
| 2018/0261922 A1 | 9/2018 | Behdad et al. | |
| 2019/0343388 A1* | 11/2019 | Bahmanyar | A61B 5/036 |

\* cited by examiner

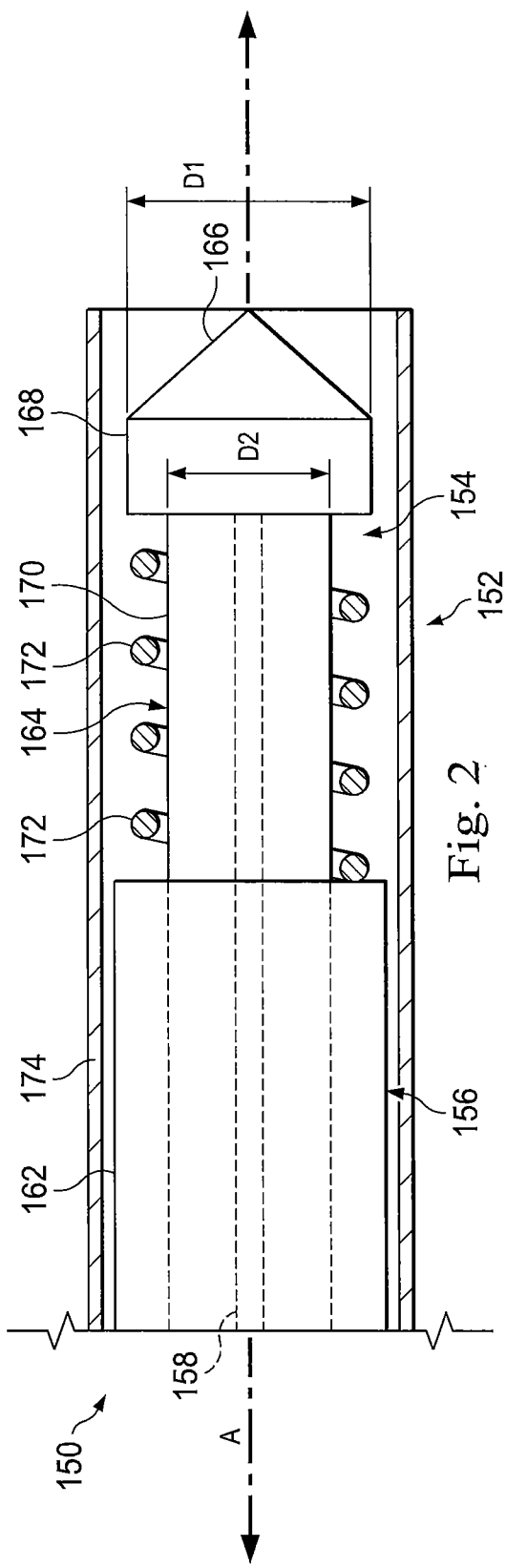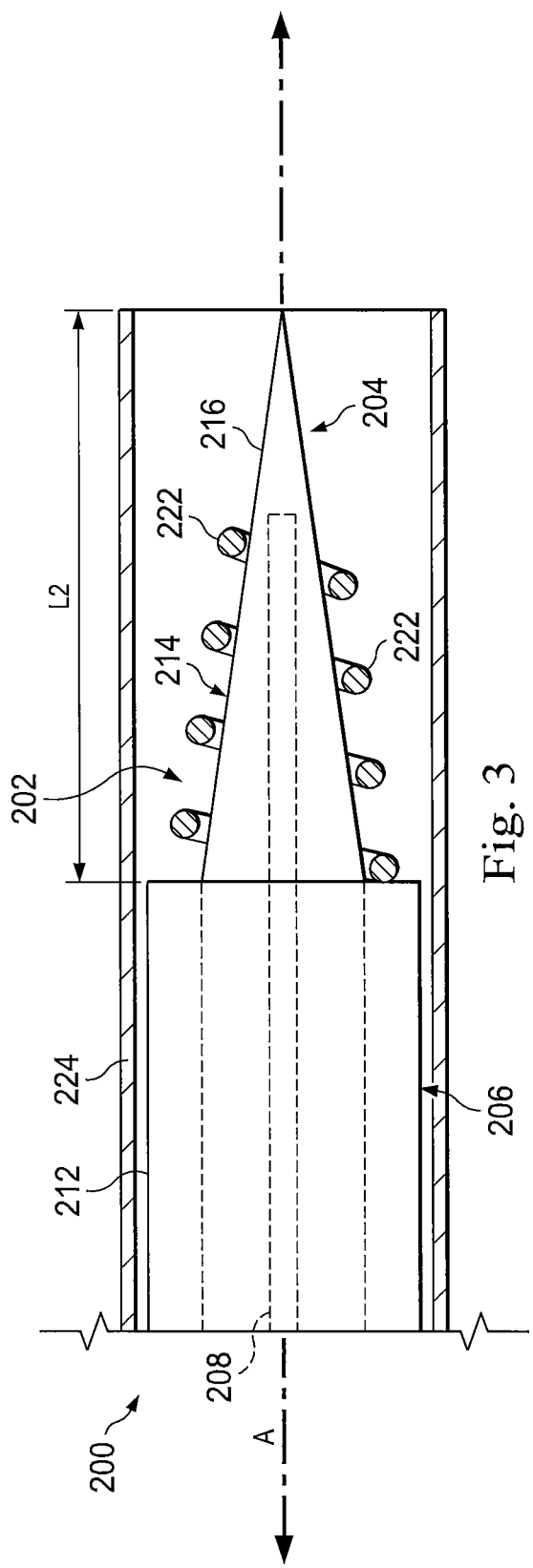

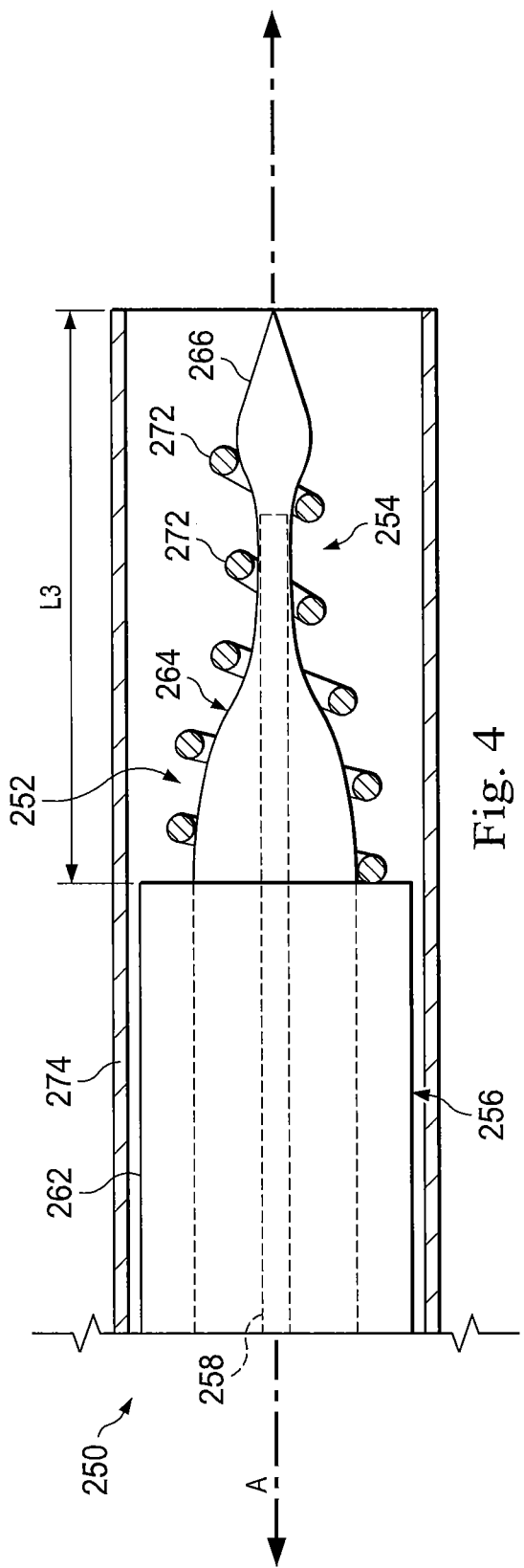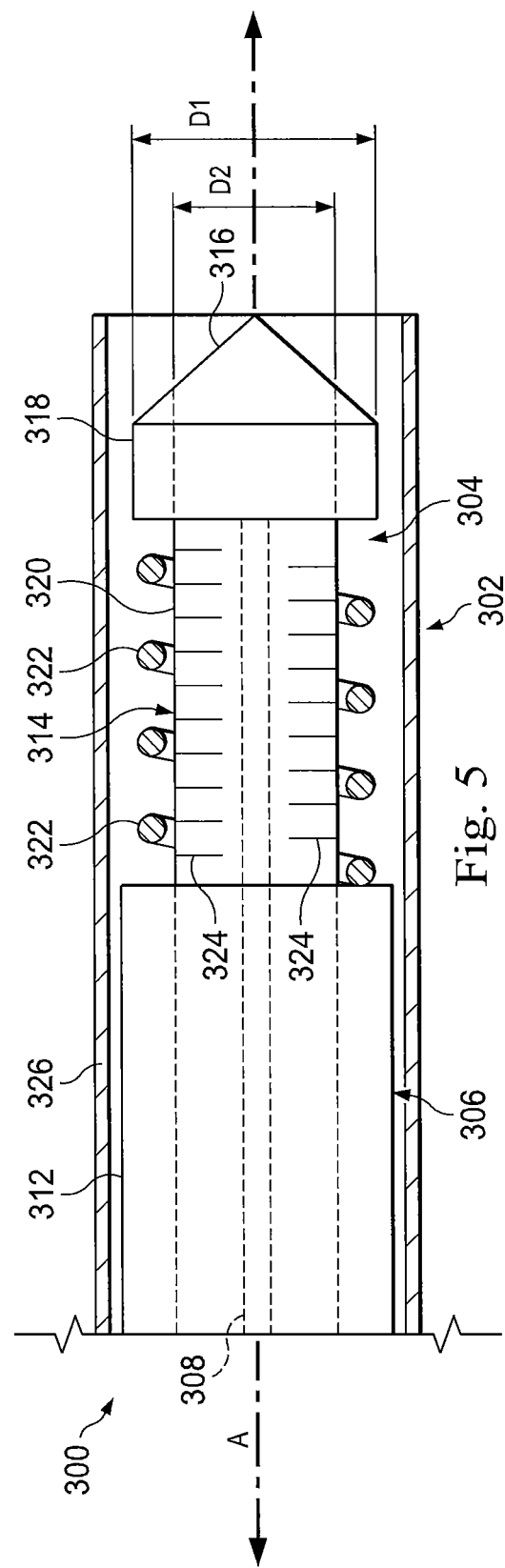

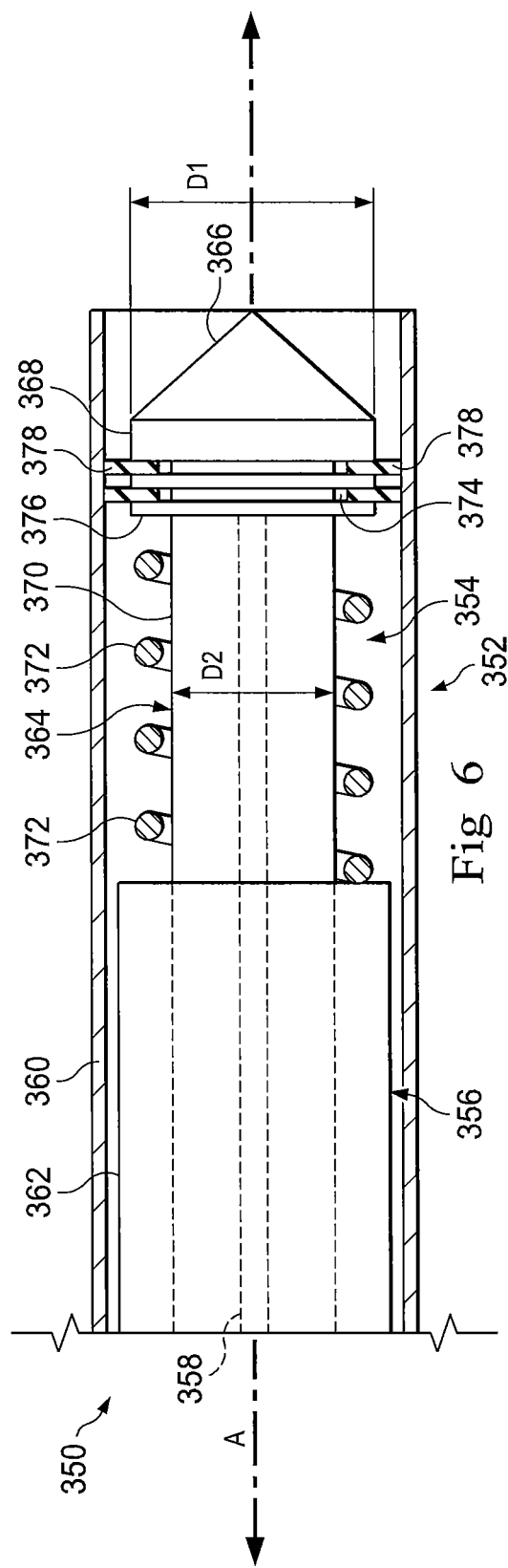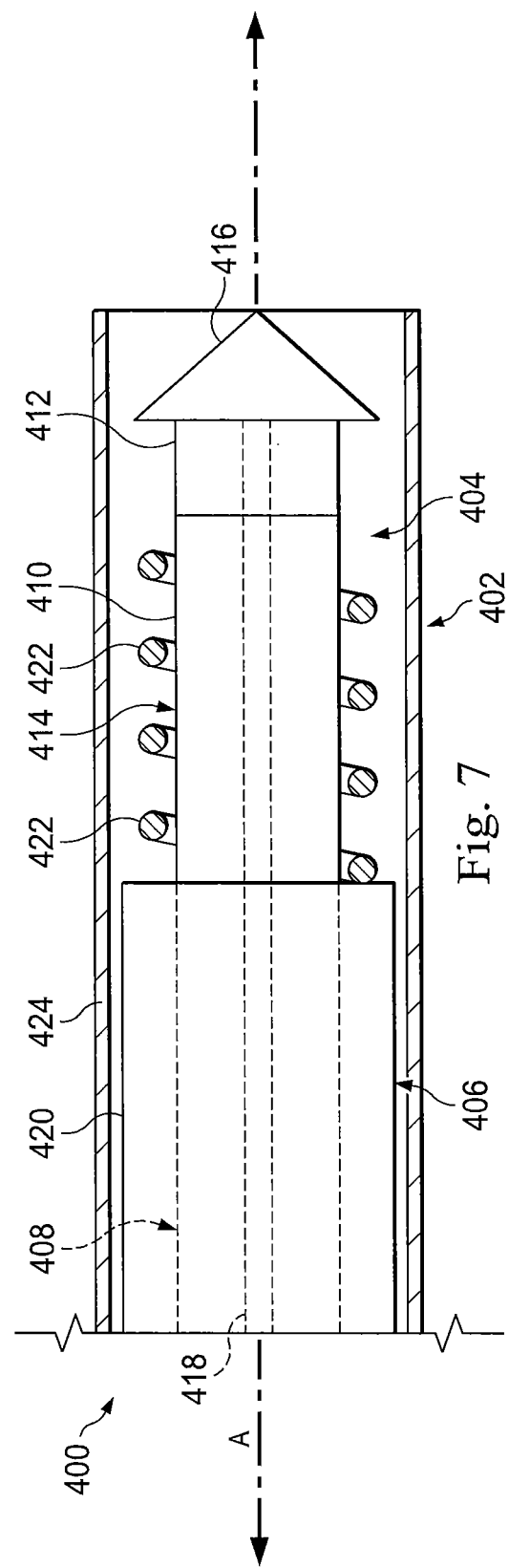

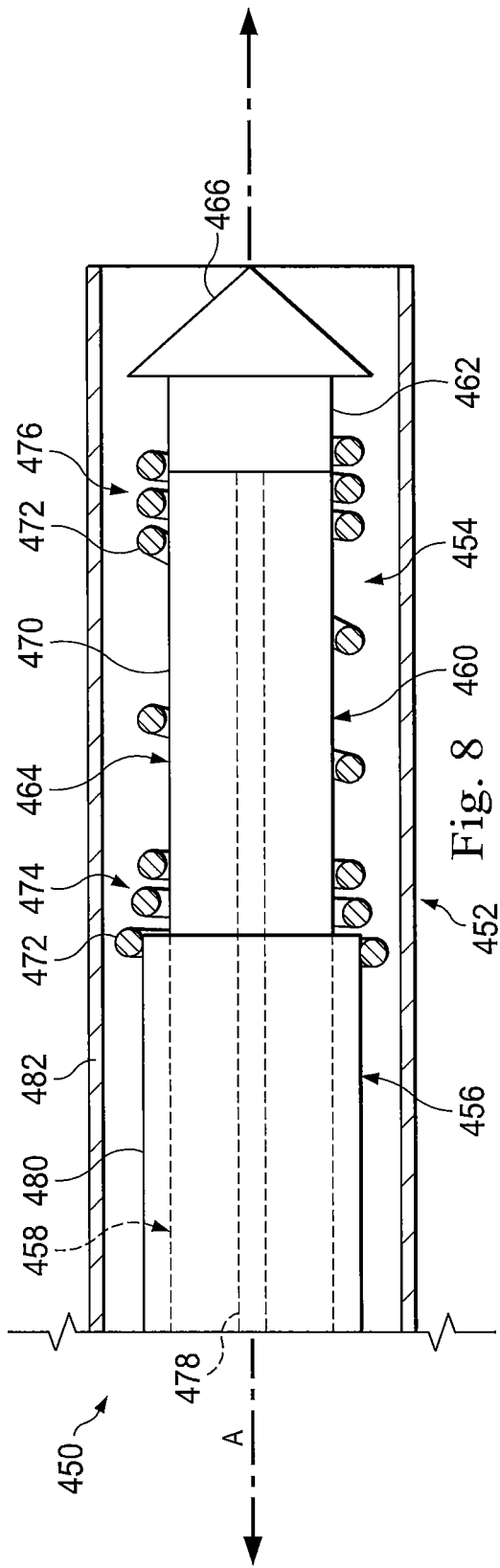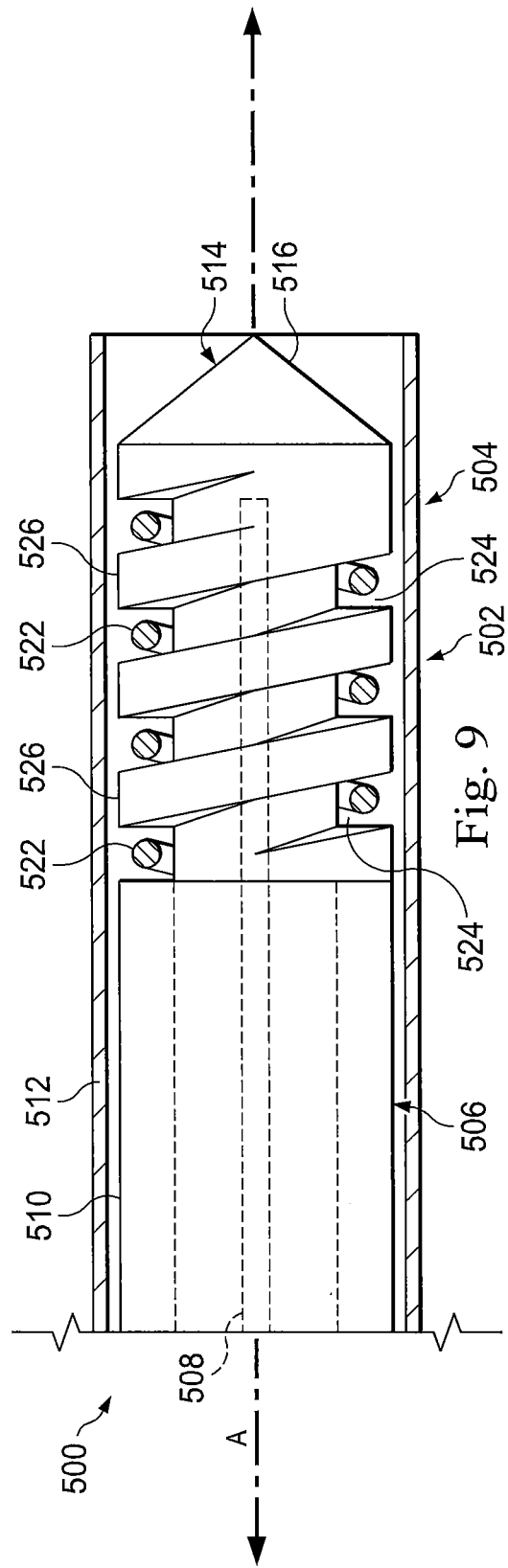

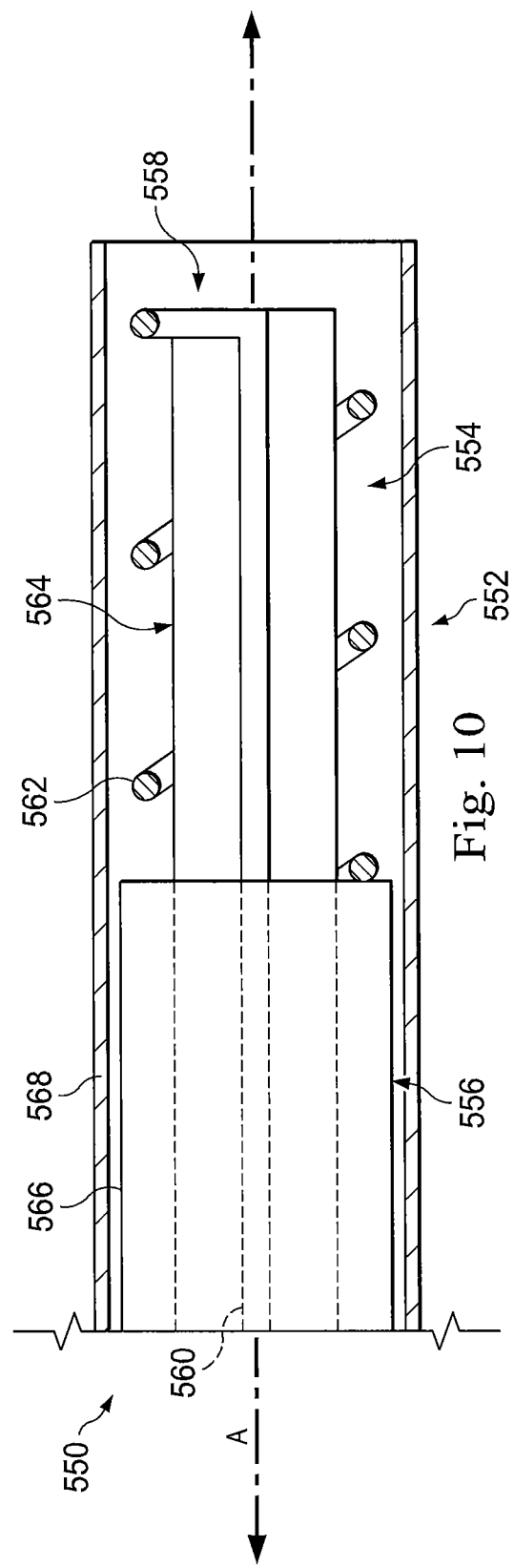

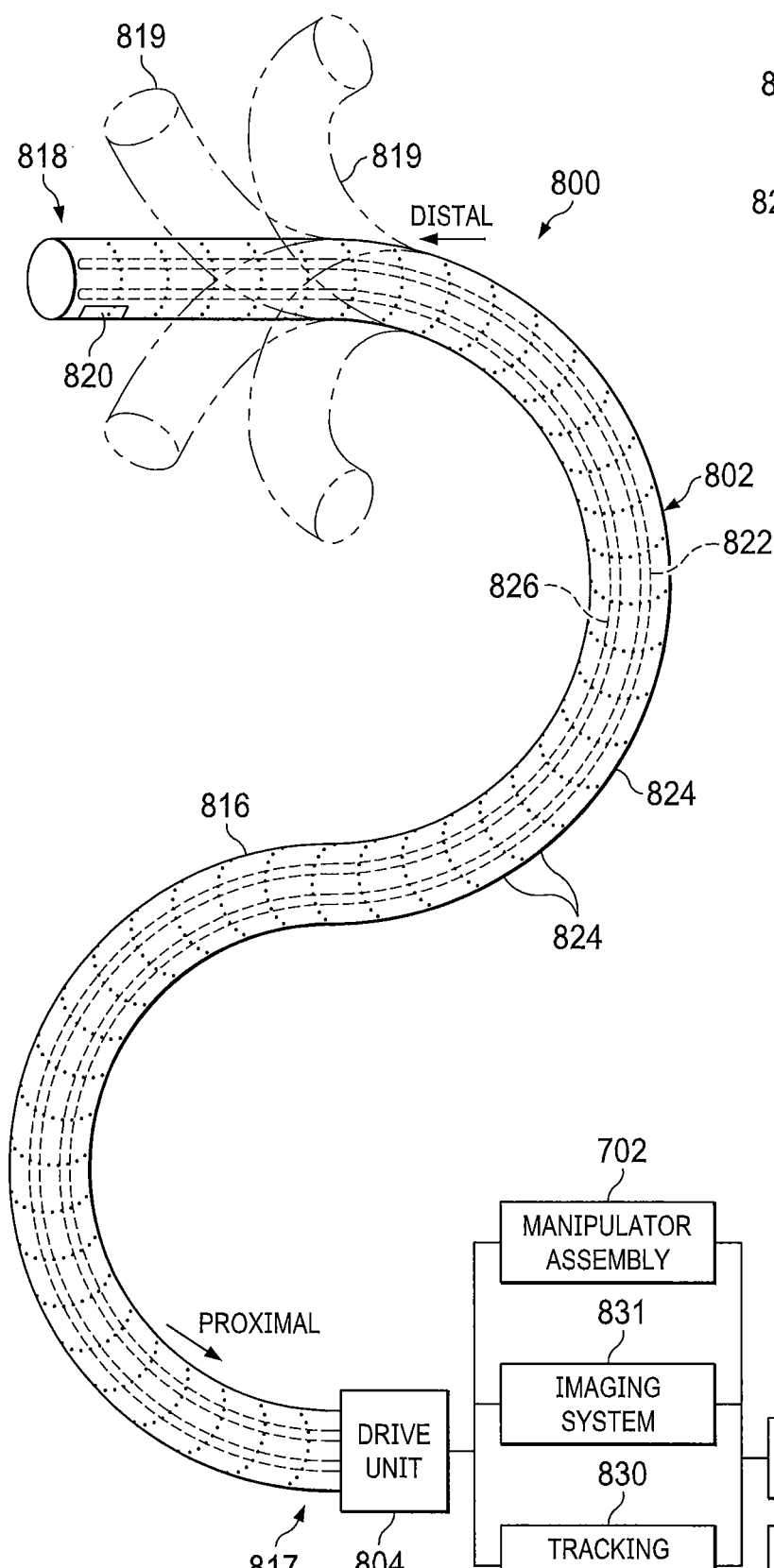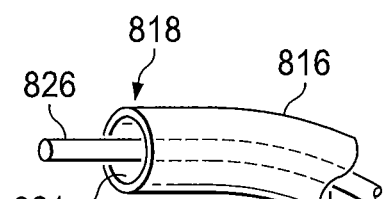
Fig. 13B
Fig. 13A

COILED DIPOLE ANTENNA

CROSS-REFERENCE TO RELATED APPLICATIONS

This application claims the benefit of U.S. Provisional Application 62/754,886 filed Nov. 2, 2018 and U.S. Provisional Application 62/844,328 filed May 7, 2019, all of which are incorporated by reference herein in their entirety.

FIELD

The present disclosure is directed to minimally invasive ablation systems and methods of use.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Minimally invasive medical tools may also include ablation instruments. Ablation instruments transmit energy in the form of electromagnetic waves to a targeted area of tissue, such as a tumor or other growth, within the patient anatomy to destroy the targeted tissue. Some minimally invasive medical tools and ablation instruments may be teleoperated or otherwise computer-assisted. Various features may improve the effectiveness of minimally invasive ablation instruments.

SUMMARY

Embodiments of the invention are best summarized by the claims that follow the description.

In some examples, an antenna system comprises a transmission member and an antenna at a distal end of the transmission member. The antenna includes a first conductive arm, an insulator extending around the first conductive arm, and a second conductive arm wound around at least a first portion of the insulator to form a second conductive arm coil. A property of the insulator varies along an insulator longitudinal axis of the insulator.

In some examples, an antenna system comprises a transmission member and an antenna at a distal end of the transmission member. The antenna includes a first conductive arm, an insulator extending around the first conductive arm, and a second conductive arm wound around at least a first portion of the insulator to form a second conductive arm coil. The second conductive arm coil is wound around the at least the first portion of the insulator providing a variable property along the length of the second conductive arm coil.

In some examples, a method of transferring energy to an ablation target site comprises conducting energy through a transmission member and radiating energy from a first conductive arm and a second conductive arm of an antenna at a distal end of the transmission member. The antenna further includes an insulator extending around the first conductive arm. The second conductive arm is wound around at least a portion of the insulator to form a second conductive arm coil.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 2 is a partial cross sectional side view of an antenna system with an insulator including a pointed tip and sections of differing radii along the insulator length according to some embodiments.

FIG. 3 is a partial cross sectional side view of an antenna system with an insulator including a taper along the insulator length according to some embodiments.

FIG. 4 is a partial cross sectional side view of an antenna system with an insulator including a pointed tip and sections of varying radii along the insulator length according to some embodiments.

FIG. 5 is a partial cross sectional side view of an antenna system with an insulator including slots along the insulator length according to some embodiments.

FIG. 6 is a partial cross sectional side view of an antenna system with an insulator including grooved portions according to some embodiments.

FIG. 7 is a partial cross sectional side view of an antenna system with an insulator including a plurality of sections with different material properties along the insulator length according to some embodiments.

FIG. 8 is a partial cross sectional side view of an antenna system with a conductive coil including a variable coil pitch according to some embodiments.

FIG. 9 is a partial cross sectional side view of an antenna system with a series of grooves sized to receive a conductive coil according to some embodiments.

FIG. 10 is a partial cross sectional side view of an antenna system with a conductive coil extending from and around an inner conductor according to some embodiments.

FIG. 13A is a simplified diagram of a medical instrument system according to some embodiments.

FIG. 13B is a simplified diagram of a medical instrument with an extended medical tool according to some embodiments.

Figure 1:
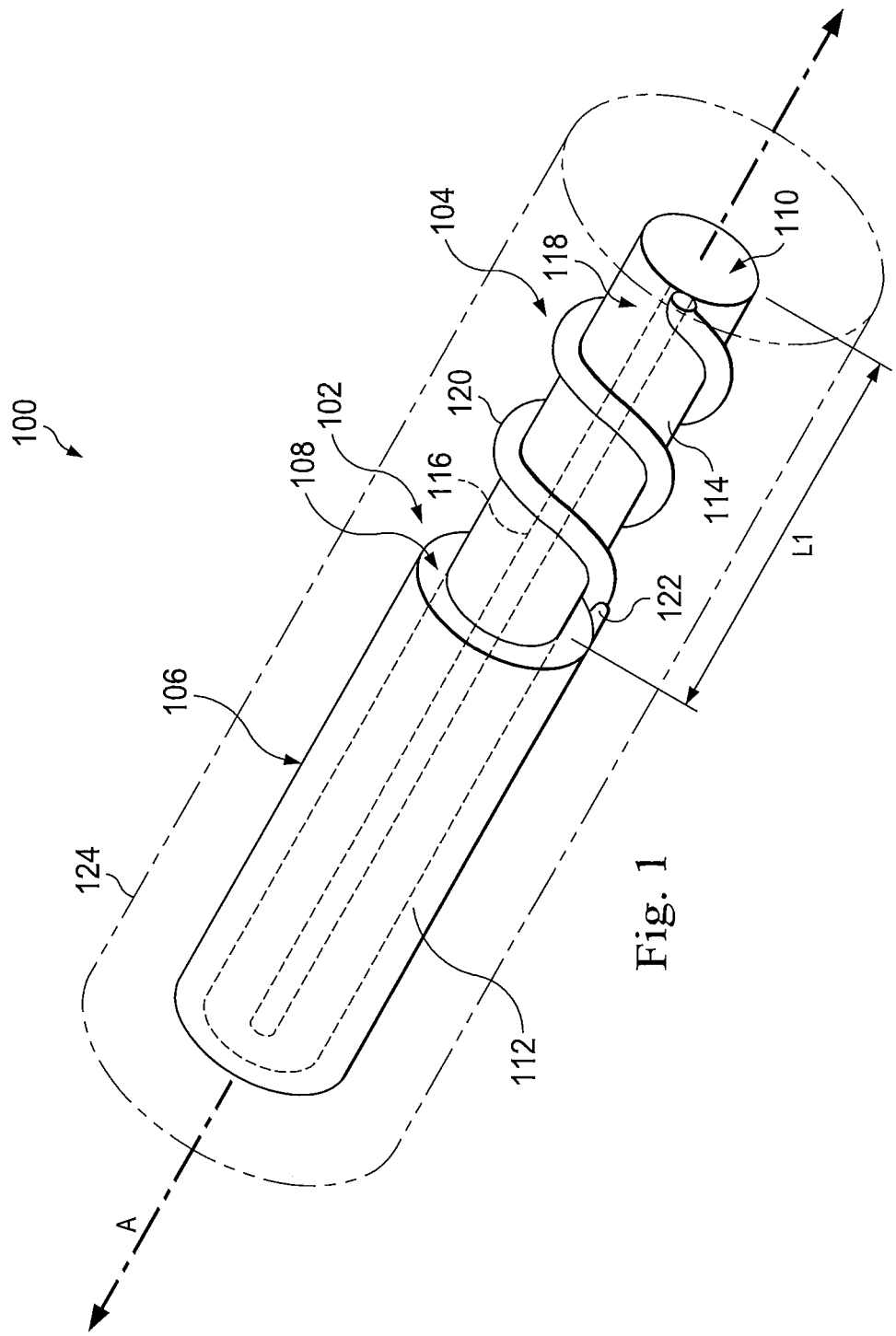
FIG. 1 is a perspective view of an antenna system for tissue ablation with an antenna coupled to a transmission member according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIGS. 1-10 illustrate various embodiments of antenna systems. In some embodiments, the antenna systems are used for tissue ablation, causing an increase in a temperature of an anatomic target area by transmitting electromagnetic waves from the antenna system to the anatomic target area, or ablation site. In some embodiments, antenna systems may be flexible and suitable for use in, for example, surgical, diagnostic, therapeutic, ablative, and/or biopsy procedures. In some embodiments, the antenna systems may be used as a medical instrument in an image-guided medical procedure performed with a teleoperated medical system as described in further detail below. While some embodiments are provided herein with respect to such procedures, any reference to medical or surgical instruments and medical or surgical methods is non-limiting. In some embodiments, the antenna systems may be used for non-teleoperational procedures involving traditional manually operated medical instruments. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As shown in FIG. 1, an antenna system 100 generally includes a flexible antenna instrument 102 which includes an antenna 104 extending from an elongate transmission member 106. The antenna 104 extends between a proximal end 108 and a distal end 110. The elongate transmission member 106 includes an outer conductor 112 at least partially surrounding an inner conductor 116. The elongate transmission member 106 also includes an insulator 114 (e.g. a dielectric layer) substantially surrounding the inner conductor 116, insulating the outer conductor 112 from the inner conductor 116. In this embodiment, the insulator 114 and the inner conductor 116 extend distally beyond the outer conductor 112. In some embodiments, a portion of the insulator 114 that extends distally beyond the outer conductor 112 may be coupled to or integrally formed and continuous with a portion of the insulator 114 that extends within the outer conductor. In this embodiment, elongate transmission member 106 is a coaxial cable but for simplicity, jacket layers and other details may not be illustrated. Other coaxial cable configurations with different configurations, shapes, etc. of inner conductor, outer conductor, and dielectric layers could also be used. In alternative embodiments, any type of elongate transmission member may be used for the antenna instrument 102. As will be described in detail below, antenna system 100 and the other antenna systems described may be constructed to provide for features including the ability of the antenna to puncture tissue, antenna flexibility to allow navigation through patient anatomy, strong material joints, and strengthened areas of antenna transition.

In this embodiment, antenna 104 is a helical dipole antenna extending along a longitudinal axis A and may be used to radiate microwave energy for use in the tissue ablation process. More specifically, antenna 104 is used to create electromagnetic radiation within a wavelength range of one meter to one millimeter, and within a frequency range of approximately 300 Megahertz (MHz) TO 300 Gigahertz (GHz) (e.g., a microwave). A microwave, which is a type of radio wave, is made up of a magnetic field at a right angle to an electric field, and both the magnetic field and the electric field oscillate at a specific frequency and travel together along a direction that is perpendicular to both the magnetic field and the electric field. In some embodiments, the wavelength and the frequency of the microwaves being radiated by antenna 104 may be modified to cause a desired type of ablation at the ablation target site.

In this embodiment, the dipole antenna 104 includes a portion 118 of inner conductor 116 distal of the outer conductor 112 as a first arm of the dipole antenna 104. A conductive coil 120 is wound around the insulator 114 surrounding the portion 118 of inner conductor 116. The coil 120, which may be a helically shaped coil, forms a second arm of the dipole antenna 104. The coil 120 may be looped around an outer perimeter of the exposed portion of insulator 114 a plurality of times to form a spiral-shape. The insulator 114 may insulate the outer conductor 112 from the inner conductor 116 and also insulate the inner conductor 116 from the coil 120. The coil 120 may be electrically coupled (e.g., soldered) to outer conductor 112 by an electrical coupling 122.

In some embodiments, the material of the insulator 114 may be chosen to provide a high axial stiffness along axis A to allow greater rigidity to puncture tissue. Rigid materials such as polyetheretherketone (PEEK) or polyetherimide (e.g. Ultem) may be used, for example, to increase stiffness in the antenna and prevent buckling during a puncture operation.

In some embodiments, the coil 120 may extend along the entire length L1 of portion 118 of the inner conductor 116 or along a substantial portion of length L1 (e.g. from 90% to 100%) to allow bending stiffness and mechanical properties of the entire antenna 104 to be uniform, particularly under bending when the antenna forms a constant curvature. In some embodiments, the coil 120 may extend only partially along the length L1 of portion 118 of the inner conductor. In some other embodiments, the coil 120 may be a double-helix coil extending along opposing sides of inner conductor 116 and insulator 114. In some other embodiments, coil 120 may wrap back over itself in an overlapped coil shape. In some embodiments, coil 120 may include two tubes wound together to create a helically wound double coil. In some embodiments, coil 120 may extend only partially along the exposed surface of inner conductor. In some other embodiments, coil 120 may wrap back over itself in an overlapped coil shape. In alternative embodiments, coil 120 may be configured in any way that facilitates operation of antenna instrument 102 as described herein.

Antenna 104 and elongate transmission member 106 are disposed within an outer jacket 124. In some embodiments the jacket 124 is closed, sealed, or otherwise restricts fluid from passing into or out of the jacket. In alternative embodiments, jacket 124 may have openings, slits, or otherwise be unsealed along any portion of jacket 124 to allow fluid to pass into the jacket or out from the jacket.

FIG. 2 is a cross sectional side view of an antenna system 150. The elements of the system 150, such as the inner conductor, the outer conductor, and the jacket, that appear similar to previously described structures with different reference numerals may be substantially similar, with differences as described. The antenna system 150 generally includes a flexible antenna instrument 152 which includes an antenna 154 extending from an elongate transmission member 156. Antenna 154 and elongate transmission member 156 are disposed within an outer jacket 174. The elongate transmission member 156 includes an outer conductor 162 at least partially surrounding an inner conductor 158. The elongate transmission member 156 also includes an insulator 164 (e.g. a dielectric layer) substantially surrounding the inner conductor 158, insulating the outer conductor 162 from the inner conductor 158. In this embodiment, the insulator 164 includes a pointed tip 166, a section 168 having a width (e.g. a diameter) D1, and a section 170 having a width (e.g. a diameter) D2. In this embodiment, D1 is larger than D2 which may help in construction of the pointed tip 166 by providing more material to form the pointed tip 166 while still maintaining a smaller overall outer diameter for the antenna 154. The pointed tip 166 may allow the antenna instrument 152 to more easily puncture anatomic tissue. A conductive coil 172 (which may be substantially similar to coil 120, with differences as described) is wrapped around the section 170 of the insulator 164 forming the second arm of the dipole antenna 154.

FIG. 3 is a cross sectional view of an antenna system 200. The elements of the system 200, such as the inner conductor, the outer conductor, and the jacket, that appear similar to previously described structures with different reference numerals may be substantially similar, with differences as described. The antenna system 200 generally includes a flexible antenna instrument 202 which includes an antenna 204 extending from an elongate transmission member 206. Antenna 204 and elongate transmission member 206 are disposed within an outer jacket 224. The elongate transmission member 206 includes an outer conductor 212 at least partially surrounding an inner conductor 208. The elongate transmission member 206 also includes an insulator 214 (e.g. a dielectric layer) substantially surrounding the inner conductor 208, insulating the outer conductor 212 from the inner conductor 208. In this embodiment, the insulator 214 is tapered, and consequently the outer profile varies, along a length L2 of the antenna 204 and includes a pointed tip 216. The pointed tip 216 may allow the antenna instrument 202 to more easily puncture anatomic tissue. Additionally, in some embodiments a smaller diameter tip, e.g. provided by a distally tapered down antenna, can provide for better tissue penetration than a larger diameter tip. In this embodiment the taper is continuous between the elongate transmission member 206 and the tip 216, but in other embodiments, only a portion of the length L2 may be tapered. A conductive coil 222 (which may be substantially similar to coil 120, with differences as described) is wrapped around the tapered insulator 214 forming the second arm of the dipole antenna 204. Thus, the radius of the coil 222 may also taper with the radius of the insulator 214.

FIG. 4 is a cross sectional view of an antenna system 250. The elements of the system 250, such as the inner conductor, the outer conductor, and the jacket, that appear similar to previously described structures with different reference numerals may be substantially similar, with differences as described. The antenna system 250 generally includes a flexible antenna instrument 252 which includes an antenna 254 extending from an elongate transmission member 256. Antenna 254 and elongate transmission member 256 are disposed within an outer jacket 274. The elongate transmission member 256 includes an outer conductor 262 at least partially surrounding an inner conductor 258. The elongate transmission member 256 also includes an insulator 264 (e.g. a dielectric layer) substantially surrounding the inner conductor 258, insulating the outer conductor 262 from the inner conductor 258. In this embodiment, the insulator 264 has a variable width (e.g. diameter), and consequently a variable outer profile, along a length L3 of the antenna 254 and includes a pointed tip 266. The varying diameter of the insulator 264 along the length L3 may provide for varied bendability along the length L3. A conductive coil 272 (which may be substantially similar to coil 120, with differences as described) is wrapped around the insulator 264 forming the second arm of the dipole antenna 254. Thus the coil 272 may also have a coil diameter that varies along length L3 to correspond with the diameter of the insulator. The pointed tip 266 may allow the antenna instrument 252 to more easily puncture anatomic tissue.

FIG. 5 is a cross sectional view of an antenna system 300. The elements of the system 300, such as the inner conductor, the outer conductor, and the jacket, that appear similar to previously described structures with different reference numerals may be substantially similar, with differences as described. The antenna system 300 generally includes a flexible antenna instrument 302 which includes an antenna 304 extending from an elongate transmission member 306. Antenna 304 and elongate transmission member 306 are disposed within an outer jacket 326. The elongate transmission member 306 includes an outer conductor 312 at least partially surrounding an inner conductor 308. The elongate transmission member 306 also includes an insulator 314 (e.g. a dielectric layer) substantially surrounding the inner conductor 308, insulating the outer conductor 312 from the inner conductor 308. In this embodiment, the insulator 314 includes a pointed tip 316, a section 318 having a width (e.g. a diameter) D1, and a section 320 having a width (e.g. a diameter) D2. In this embodiment, D1 is larger than D2 which may aid in construction of the pointed tip 316 by providing more material to form the pointed tip 316 while still maintaining a smaller overall outer diameter for the antenna instrument 302. The pointed tip 316 may allow the antenna instrument 302 to more easily puncture anatomic tissue. A conductive coil 322 (which may be substantially similar to coil 120, with differences as described) is wrapped around the section 320 of the insulator 314 forming the second arm of the dipole antenna 304. The section 320 of the insulator 314 may include one or more slots 324 to provide flexibility to the insulator, allowing for delivery of the antenna instrument through tortuous anatomy and tight bends within an anatomical path. In some embodiments the slots 324 may be laser cut. In various embodiments the slots 324 may include a continuous spiral slot, multiple co-axial spiral slots, radial ring slots, H-patterned slots, curved pattern slots, or any other configurations of slots or sets of formed patterns that provides the desired flexibility to the antenna. The formed patterns may be created, for example, by laser cutting or injection molding. In some embodiments, the slots 324 may extend along only a portion, and not the entire length, of the section 320.

FIG. 6 is a cross sectional view of an antenna system 350. The elements of the system 350, such as the inner conductor, the outer conductor, and the jacket, that appear similar to previously described structures with different reference numerals may be substantially similar, with differences as described. The antenna system 350 generally includes a flexible antenna instrument 352 which includes an antenna 354 extending from an elongate transmission member 356. Antenna 354 and elongate transmission member 356 are disposed within an outer jacket 360. The elongate transmission member 356 includes an outer conductor 362 at least partially surrounding an inner conductor 358. The elongate transmission member 356 also includes an insulator 364 (e.g. a dielectric layer) substantially surrounding the inner conductor 358, insulating the outer conductor 362 from the inner conductor 358. In this embodiment, the insulator 364 includes a pointed tip 366, a section 368 having a width (e.g. a diameter) D1, and a section 370 having a width (e.g. a diameter) D2. In this embodiment, D1 is larger than D2 which may aid in construction of the pointed tip 316 by providing more material to form the pointed tip 316 while still maintaining a smaller overall outer diameter for the antenna instrument 352. The pointed tip 366 may allow the antenna instrument 352 to more easily puncture anatomic tissue. A conductive coil 372 (which may be substantially similar to coil 120, with differences as described) is wrapped around the section 370 of the insulator 364 forming the second arm of the dipole antenna 354. In this embodiment the section 368 of the insulator 364 includes a pattern of grooves 374 and protrusions 376. An adhesive insulation material 378, which may be the same or similar to the material forming the insulator 364, may be melted or otherwise flowed into the grooves 374 between the protrusions 376 to adhere the outer jacket 360 to the insulator 364. In another embodiment, the jacket 360 can be adhered to the insulator 364, by additionally varying the material composition of the insulator 364. By blending from a material that may be more suitable mechanically or from a temperature perspective, to a material more similar to the jacket 360 at a distal end of the jacket 360, a good bonding surface can be formed between the jacket 360 and the insulator 364. For example, a blend from a fluoropolymer to nylon with fluoropolymer impregnated could be suitable. In some embodiments, the insulation material 378 adhered between the jacket 360 and the insulator 364 may provide a waterproof layer or barrier around the insulator 364. In alternative embodiments, the grooves and protrusions may be replaced or supplemented with surface treatments to an outer wall of the section 368 to provide a waterproof layer or barrier around the insulator 364. In alternative embodiments, a jacket may be bonded or otherwise interfaced to an insulator after one or the other of the jacket or insulator undergoes a phase change, such as softening or melting.

FIG. 7 is a cross sectional view of an antenna system 400. The elements of the system 400, such as the inner conductor, the outer conductor, and the jacket, that appear similar to previously described structures with different reference numerals may be substantially similar, with differences as described. The antenna system 400 generally includes a flexible antenna instrument 402 which includes an antenna 404 extending from an elongate transmission member 406. Antenna 404 and elongate transmission member 406 are disposed within an outer jacket 424. The elongate transmission member 406 includes an outer conductor 420 at least partially surrounding an inner conductor 418. The elongate transmission member 406 also includes an insulator 414 (e.g. a dielectric layer) substantially surrounding the inner conductor 418, insulating the outer conductor 420 from the inner conductor 418. A conductive coil 422 (which may be substantially similar to coil 120, with differences as described) is wrapped around the insulator 414 forming the second arm of the dipole antenna 404.

In this embodiment, the insulator 414 may be formed from sections of differing materials to vary the stiffness of the insulator along the axis A. In this embodiment, the insulator 414 may include a proximal section 408 located within the outer conductor 420 and a medial section 410 to or integrally formed with the section 408 that extends distally beyond the outer conductor 420. The insulator 414 may also include a distal section 412 including a pointed tip 416, where the distal section 412 can be coupled to or integrally formed with the medial section 410. The proximal section 408 may be formed of a material that is less stiff than the material used to form medial section 410 and/or distal section 412. The may allow the antenna instrument 402 to be sufficiently flexible along its proximal length to permit bending and articulation when deployed within a patient anatomy (e.g. tortuous patient anatomy including tight bends within an anatomical path). The medial section 410 may be a transition region formed of a material that is stiffer than the material forming proximal section 408 but less stiff than the material forming distal section 412 which may be formed of a stiff or hardened material. In another embodiment, the medial section 410 may be a blend of the material forming proximal section 408 and the material forming distal section 412. With any of these material constructions, the antenna instrument 402 may have proximal flexibility to facilitate navigation in tortuous anatomy while still providing distal rigidity to facilitate puncturing of anatomic tissue. In alternative embodiments, there may be more or fewer regions of varying stiffness.

In alternative embodiments, the conductive coil may have variable properties along its length. For example, the variable property may be a cross section of the wire forming the conductive coil. The cross section may vary along the length of the coil such that the cross section is non-constant. As another example, the variable property may be a material property of the conductive coil that varies along the length of the coil such that the material property is non-constant. The variable material property may include any physical, mechanical, or chemical property, including for example material composition, elasticity, strength, or density.

FIG. 8 is a cross sectional view of an antenna system 450. The elements of the system 450, such as the inner conductor, the outer conductor, and the jacket, that appear similar to previously described structures with different reference numerals may be substantially similar, with differences as described. The antenna system 450 generally includes a flexible antenna instrument 452 which includes an antenna 454 extending from an elongate transmission member 456. Antenna 454 and elongate transmission member 456 are disposed within an outer jacket 482. The elongate transmission member 456 includes an outer conductor 480 at least partially surrounding an inner conductor 478. The elongate transmission member 456 also includes an insulator 464 (e.g. a dielectric layer) substantially surrounding the inner conductor 478, insulating the outer conductor 480 from the inner conductor 478. In this embodiment, the insulator 464 may be formed from sections of differing materials to vary the stiffness of the insulator along the axis A. In this embodiment, the insulator 464 may include a proximal section 458 located within the outer conductor 480 and a medial section 460 coupled to or integrally formed with the proximal section 458 that extends distally beyond the outer conductor 480. The insulator 464 may also include a distal section 462 including a pointed tip section 466, where the distal section 462 can be coupled to or integrally formed with the medial section 460. The proximal section 458, medial section 460, and distal section 462 may be formed of different types of materials with different stiffnesses, as previously described. In this embodiment, a conductive coil 472 (which may be substantially similar to coil 120, with differences as described) is wrapped around the section 470 of the insulator 464 forming the second arm of the dipole antenna 454. In this embodiment, the loops of the coil 472 may vary in pitch (e.g., the distance between a helical coil's adjacent loops) along the axis A and thus may be non-constant along the length. The pitch may be non-constant along the antenna length and may vary linearly, logarithmically, according to a step function, based on another type of pattern or progression, or may be a combination of varying patterns. Since sudden changes in axial or bending stiffness may result in stress points, which can be a points of device failure, variations in the coil pitch may be used to transition axial and bending stiffness gradually along the axis A, minimizing points of stress. In this embodiment, for example, the coil 472 has a smaller pitch is the areas 474, 476 which represent transition areas between proximal section 458 and medial section 460 and medial section 460 and distal section 462, respectively. Between areas 474 and 476, the pitch of coil 472 may be larger (i.e. the loops having a greater spacing). The tighter pitch overlapping the transition point in the areas 474, 476 may provide support, acting as a collar to support and hold connections between sections of differing materials (e.g. between the medial section 460/insulator 464 and proximal section 458/outer conductor 112 and the medial section 460/insulator 464 and distal section 462/pointed tip 466 respectively). In some embodiments, the loops of the coil 472 may be soldered together to provide additional rigidity in the transition areas 474, 476.

FIG. 9 is a cross sectional view of an antenna system 500. The elements of the system 500, such as the inner conductor, the outer conductor, and the jacket, that appear similar to previously described structures with different reference numerals may be substantially similar, with differences as described. The antenna system 500 generally includes a flexible antenna instrument 502 which includes an antenna 504 extending from an elongate transmission member 506. Antenna 504 and elongate transmission member 506 are disposed within an outer jacket 512. The elongate transmission member 506 includes an outer conductor 510 at least partially surrounding an inner conductor 508. The elongate transmission member 506 also includes an insulator 514 (e.g. a dielectric layer) substantially surrounding the inner conductor 508, insulating the outer conductor 510 from the inner conductor 508. In this embodiment, the insulator 514 includes a pointed tip 516 that may allow the antenna instrument 502 to more easily puncture anatomic tissue. In this embodiment the insulator 514 includes a helical groove 524 and patterned protrusions 526 to hold a wound conductive coil 522. The wound conductive coil 522 forms the second arm of the dipole antenna 504. The conductive coil 522 may be substantially similar to coil 120, with differences as described. In some embodiments, the coil 522 may be installed into the groove 524, between the protrusions 526, by winding the spring onto the insulator 514 within the groove 524 from either the distal or proximal end of the groove 524 prior to forming or installation of the pointed tip 516 or the outer conductor 112. As the antenna instrument 502 is navigated through a patient anatomy and the antenna 504 bends, the groove 524 and protrusions 526 may keep the coil in position including maintaining a predetermined pitch, as defined by the groove 524, and prevent the spacing between adjacent loops of the coil 522 from changing. In some embodiments, the predetermined pitch is a uniform pitch providing for equal spacing between adjacent coils. In alternative embodiments, the predetermined pitch may be a variable pitch with varied spacing between adjacent coils which can achieve varying stiffness in the antenna along the length of the antenna. In alternative embodiments, a plurality of grooves may accommodate multiple coils of an antenna. In alternative embodiments, the pitch of the coil may be maintained by other retention features such as holding tabs, covered channels, or adhesives.

FIG. 10 is a cross sectional view of an antenna system 550. The elements of the system 550, such as the inner conductor, the outer conductor, and the jacket, that appear similar to previously described structures with different reference numerals may be substantially similar, with differences as described. The antenna system 550 generally includes a flexible antenna instrument 552 which includes an antenna 554 extending from an elongate transmission member 556. The elongate transmission member 556 includes an outer conductor 566 at least partially surrounding an inner conductor 560. The elongate transmission member 556 also includes an insulator 564 (e.g. a dielectric layer) substantially surrounding the inner conductor 560, insulating the outer conductor 566 from the inner conductor 560. A conductive coil 562 (which may be substantially similar to coil 120, with differences as described) is wrapped around the insulator 564. In this embodiment, the conductive coil 562 may be an extension of the inner conductor 560. The inner conductor 560, formed from a wire extending through the outer conductor 566, may form a first arm of the dipole antenna 554 along the length of the antenna between the outer conductor 566 and a distal end 558. The first arm of the dipole antenna 554 can be substantially surrounded by the insulator 564. The wire forming the inner conductor 560 may then extend from the insulator 564 at the distal end 558 and be looped back and wound in a proximal direction around the insulator 564 to form a second arm of the dipole antenna 554. Thus, the inner conductor 560 is coupled to and continuous with the second conductive arm (e.g., conductive coil 562). Winding the wire to form both the first arm and second arm of the dipole antenna 554 can provide for a shorter length antenna 554, creating a more circular ablation zone within tissue which can be desirable in some embodiments. In an alternative embodiment, the inner and outer conductors may be electrically connected if the length of the antenna is a multiple of [lambda/4+(n+1)]×[lambda/4]. In some embodiments (not shown in FIG. 10), the insulator 564 can extend further to form a pointed tip or a pointed tip may be fixed to the distal end 558 of the insulator 564.

Any of the various features of FIGS. 2-10 may be used in combination in alternative antenna systems.

Figure 11:
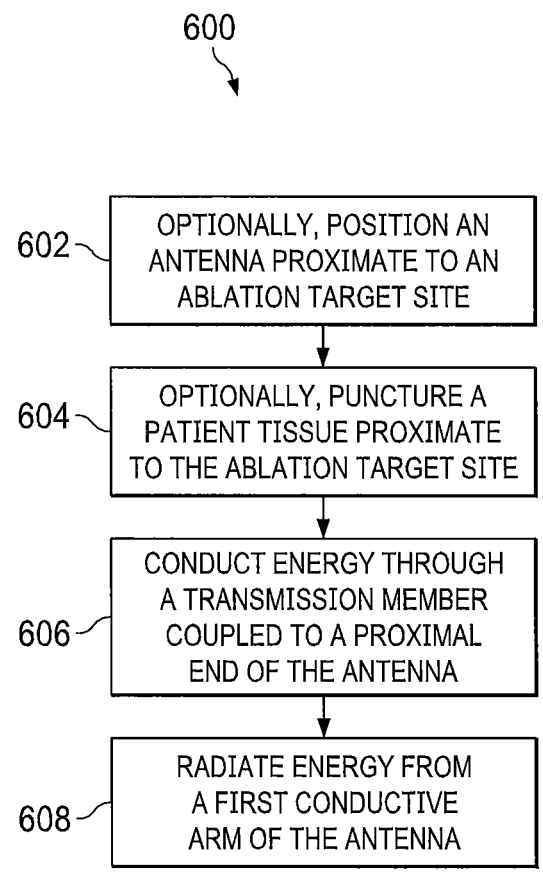
FIG. 11 is a flowchart illustrating a method of ablation according to some embodiments.

FIG. 11 illustrates a method 600 for transferring energy to an ablation target site according to some embodiments. The method 600 is illustrated as a set of operations or processes 602 through 608. Not all of the illustrated processes 602 through 608 may be performed in all embodiments of method 600. Additionally, one or more processes that are not expressly illustrated in FIG. 11 may be included before, after, in between, or as part of the processes 602 through 608. In some embodiments, one or more of the processes 602 through 608 may be implemented, at least in part, in the form of executable code stored on non-transitory, tangible, machine-readable media that when run by one or more processors (e.g., the processors of a control system) may cause the one or more processors to perform one or more of the processes. In one or more embodiments, the one or more of the processes may be performed by a control system (e.g., control system 712).

At an optional process 602, an antenna, such as dipole antenna 104 or any of the previously described antennas, may be positioned at or near a target site to perform an ablation. As described in the embodiments above, an antenna may be coupled to a distal end of an elongated transmission member. At an optional process 604, the antenna may be used to puncture the patient tissue proximate to the target site. At a process 606, energy may be conducted through the transmission member to the antenna. At a process 608, energy may be radiated from a first conductive arm of the antenna to ablate the patient tissue.

Figure 14:
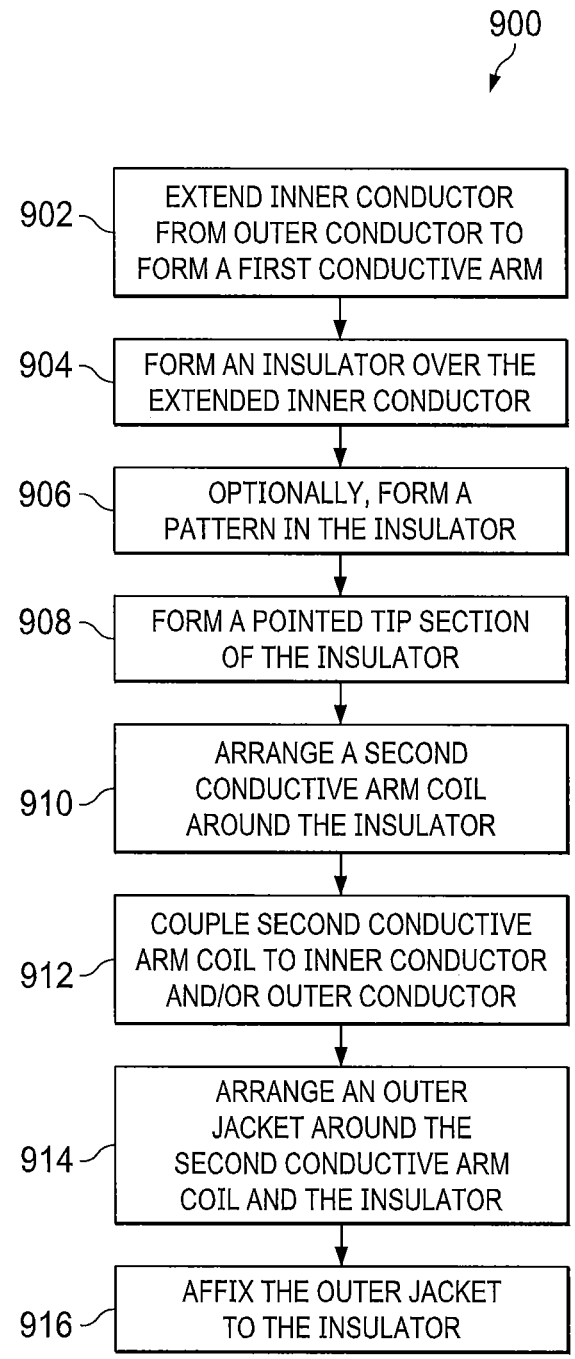
FIG. 14 is a flowchart illustrating a method of manufacturing an antenna system according to some embodiments.

FIG. 14 illustrates a method 900 for manufacturing an antenna system such as any of the previously described antenna systems. The method 900 is illustrated as a set of operations or processes, but not all of the illustrated processes may be performed in all embodiments of method 900. Additionally, one or more processes that are not expressly illustrated in FIG. 14 may be included before, after, in between, or as part of the illustrated processes. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes. In one or more embodiments, the one or more of the processes may be performed by a control system (e.g., control system 712).

At a process 902, an inner conductor (e.g., inner conductor 116 or others previously described) is extended from an outer conductor (e.g., outer conductor 112 or others previously described) to form a first conductive arm. In some embodiments, the inner and outer conductors may be components of a coaxial cable. At a process 904, an insulator (e.g., insulator 114 or others previously described) may be formed over the extended inner conductor. In some embodiments, the insulator formed over the extended inner conductor may be coupled (e.g. mechanically or adhesively) to a portion of the insulator that extends within the outer conductor. In other embodiments, the insulator formed over the extended inner conductor may be integrally and continuously formed with the portion of the insulator that extends within the outer conductor.

At an optional process 906, patterns are formed in the insulator such as by laser cutting or by injection molding. In some embodiments the pattern may be a groove, a continuous spiral slot, multiple co-axial spiral slots, radial ring slots, H-patterned slots, curved pattern slots, or any other configurations of slots or sets of formed patterns that provides a desired flexibility, coil retention features, and/or adhesion features to the antenna may be generated during the process 904. At a process 908, a pointed tip section is formed on the insulator. The pointed tip section may be formed with the insulator during the process 904 or may coupled to the insulator afterward by mechanical or adhesive bonds. At a process 910, a second conductive arm coil (e.g., coil 120 or others previously described) is arranged around the insulator. In some embodiments, the second conductive arm may be wound around the insulator or wound into a pre-formed groove. In some embodiments, the coil may be pre-wound and arranged around the insulator by sliding or threaded coupling. In some embodiments, the second conductive arm coil may be an extension of the first conductive arm coil looped back and coiled around the insulator.

At a process 912, the second conductive arm coil is electrically coupled to the inner and/or outer conductor. For example, a distal end of the second conductive arm coil may be soldered to a distal end of the inner conductor, and a proximal end of the second conductive arm coil may be soldered to the inner and/or outer conductor. At a process 914, an outer jacket (e.g., outer jacket 124 or others previously described) is arranged around the second conductive arm coil and the insulator. At a process 916, the outer jacket is affixed to the insulator using any other the techniques previously described including applying an adhesive or melting the outer jacket into grooved on the insulator.

Figure 12:
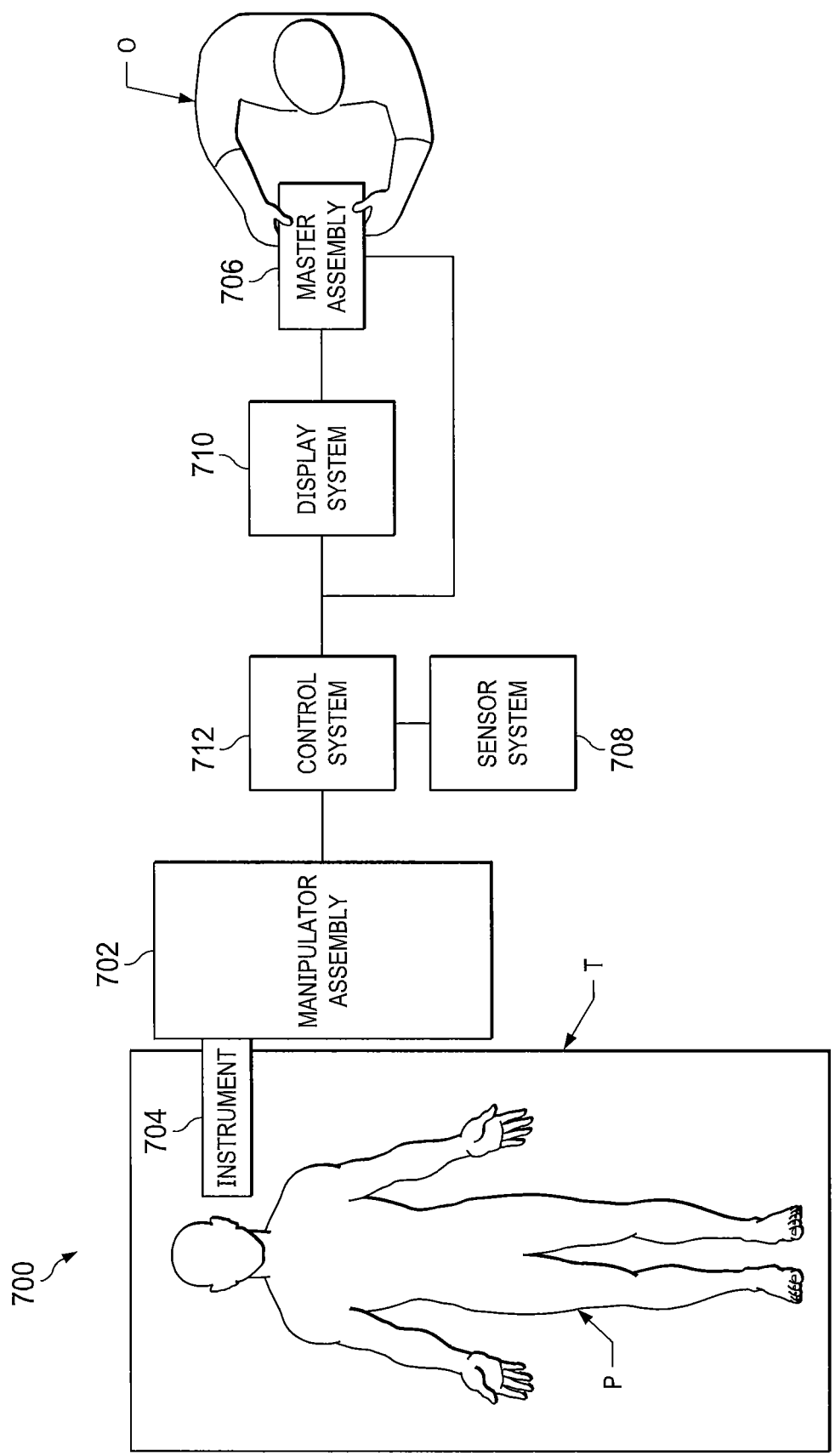
FIG. 12 is a simplified diagram of a teleoperated medical system according to some embodiments.

In various embodiments, any of the described antenna systems may be may be used as a medical instrument delivered by, coupled to, and/or controlled by a teleoperated medical system. FIG. 12 is a simplified diagram of a teleoperated medical system 700 according to some embodiments. In some embodiments, teleoperated medical system 700 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 12, medical system 700 generally includes a manipulator assembly 702 for operating a medical instrument 704 in performing various procedures on a patient P positioned on a table T. In some embodiments, the medical instrument 704 may include, deliver, couple to, and/or control any of the antenna instruments described herein. The manipulator assembly 702 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Master assembly 706 generally includes one or more control devices for controlling manipulator assembly 702. Manipulator assembly 702 supports medical instrument 704 and may optionally include a plurality of actuators or motors that drive inputs on medical instrument 704 in response to commands from a control system 712. The actuators may optionally include drive systems that when coupled to medical instrument 704 may advance medical instrument 704 into a naturally or surgically created anatomic orifice. Other drive systems may move the distal end of medical instrument 704 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 704 for grasping tissue in the jaws of a biopsy device and/or the like. Actuator position sensors such as resolvers, encoders, potentiometers, and other mechanisms may provide sensor data to medical system 700 describing the rotation and orientation of the motor shafts. This position sensor data may be used to determine motion of the objects manipulated by the actuators.

Teleoperated medical system 700 also includes a display system 710 for displaying an image or representation of the surgical site and medical instrument 704 generated by subsystems of sensor system 708 and/or any auxiliary information related to a procedure including information related to ablation (e.g. temperature, impedance, energy delivery power levels, frequency, current, energy delivery duration, indicators of tissue ablation, etc.). Display system 710 and master assembly 706 may be oriented so operator O can control medical instrument 704 and master assembly 706 with the perception of telepresence.

In some embodiments, medical instrument 704 may include components of an imaging system, which may include an imaging scope assembly or imaging instrument that records a concurrent or real-time image of a surgical site and provides the image to the operator or operator O through one or more displays of medical system 700, such as one or more displays of display system 710. The concurrent image may be, for example, a two or three-dimensional image captured by an imaging instrument positioned within the surgical site. In some embodiments, the imaging system includes endoscopic imaging instrument components that may be integrally or removably coupled to medical instrument 704. However, in some embodiments, a separate endoscope, attached to a separate manipulator assembly may be used with medical instrument 704 to image the surgical site. In some embodiments, the imaging system includes a channel (not shown) that may provide for a delivery of instruments, devices, catheters, and/or the antenna instruments described herein. The imaging system may be implemented as hardware, firmware, software or a combination thereof which interact with or are otherwise executed by one or more computer processors, which may include the processors of the control system 712.

Teleoperated medical system 700 may also include control system 712. Control system 712 includes at least one memory and at least one computer processor (not shown) for effecting control between medical instrument 704, master assembly 706, sensor system 708, and display system 710. Control system 712 also includes programmed instructions (e.g., a non-transitory machine-readable medium storing the instructions) to implement some or all of the methods described in accordance with aspects disclosed herein, including instructions for providing information to display system 710.

Control system 712 may optionally further include a virtual visualization system to provide navigation assistance to operator O when controlling medical instrument 704 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

FIG. 13A is a simplified diagram of a medical instrument system 800 according to some embodiments. Medical instrument system 800 includes elongate device 802, such as a flexible catheter, coupled to a drive unit 804. Elongate device 802 includes a flexible body 816 having proximal end 817 and distal end or tip portion 818. Medical instrument system 800 further includes a tracking system 830 for determining the position, orientation, speed, velocity, pose, and/or shape of distal end 818 and/or of one or more segments 824 along flexible body 816 using one or more sensors and/or imaging devices as described in further detail below.

Tracking system 830 may optionally track distal end 818 and/or one or more of the segments 824 using a shape sensor 822. Shape sensor 822 may optionally include an optical fiber aligned with flexible body 816 (e.g., provided within an interior channel (not shown) or mounted externally). The optical fiber of shape sensor 822 forms a fiber optic bend sensor for determining the shape of flexible body 816. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. In some embodiments, tracking system 830 may optionally and/or additionally track distal end 818 using a position sensor system 820. Position sensor system 820 may be a component of an EM sensor system with position sensor system 820 including one or more conductive coils that may be subjected to an externally generated electromagnetic field. In some embodiments, position sensor system 820 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, an optical fiber sensor may be used to measure temperature or force. In some embodiments, a temperature sensor, a force sensor, an impedance sensor, or other types of sensors may be included within the flexible body.

Flexible body 816 includes a channel 821 sized and shaped to receive a medical instrument 826. In various embodiments, any of the antenna instruments described above may be inserted through the channel 821 of the flexible body 816. FIG. 13B is a simplified diagram of flexible body 816 with medical instrument 826 extended according to some embodiments. In some embodiments, medical instrument 826 may be used for procedures such as imaging, visualization, surgery, biopsy, ablation, illumination, irrigation, or suction. Medical instrument 826 can be deployed through channel 821 of flexible body 816 and used at a target location within the anatomy. Medical instrument 826 may include, for example, image capture probes, biopsy instruments, laser ablation fibers, and/or other surgical, diagnostic, or therapeutic tools. Medical instrument 826 may be used with an imaging instrument (e.g., an image capture probe) also within flexible body 816. The imaging instrument may include a cable coupled to the camera for transmitting the captured image data. In some examples, the imaging instrument may be a fiber-optic bundle, such as a fiberscope, that couples to image processing system 831. The imaging instrument may be single or multi-spectral, for example capturing image data in one or more of the visible, infrared, and/or ultraviolet spectrums. Medical instrument 826 may be advanced from the opening of channel 821 to perform the procedure and then retracted back into the channel when the procedure is complete. Medical instrument 826 may be removed from proximal end 817 of flexible body 816 or from another optional instrument port (not shown) along flexible body 816.

Flexible body 816 may also house cables, linkages, or other steering controls (not shown) that extend between drive unit 804 and distal end 818 to controllably bend distal end 818 as shown, for example, by broken dashed line depictions 819 of distal end 818. In some examples, at least four cables are used to provide independent "up-down" steering to control a pitch of distal end 818 and "left-right" steering to control a yaw of distal end 818. Steerable elongate devices are described in detail in U.S. patent application Ser. No. 13/274,208 (filed Oct. 14, 2011) (disclosing "Catheter with Removable Vision Probe"), which is incorporated by reference herein in its entirety.

The information from tracking system 830 may be sent to a navigation system 832 where it is combined with information from image processing system 831 and/or the preoperatively obtained models to provide the operator with real-time position information. In some examples, the real-time position information may be displayed on display system 710 of FIG. 12 for use in the control of medical instrument system 800. In some examples, control system 712 of FIG. 12 may utilize the position information as feedback for positioning medical instrument system 800. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 800 may be teleoperated within medical system 700 of FIG. 12. In some embodiments, manipulator assembly 706 of FIG. 12 may be replaced by direct operator control. In some examples, the direct operator control may include various handles and operator interfaces for hand-held operation of the instrument.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Medical tools that may be delivered through the flexible elongate devices or catheters disclosed herein may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between its proximal and distal ends to controllably bend the distal end of antenna instrument 102. Steerable instruments are described in detail in U.S. Pat. No. 7,416,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The systems described herein may be suited for navigation and treatment of anatomic tissues, via natural or surgically created connected passageways, in any of a variety of anatomic systems, including the lung, colon, stomach, the intestines, the kidneys and kidney calices, bladder, liver, gall bladder, pancreas, spleen, the ureter, ovaries, uterus, the brain, the circulatory system including the heart, vasculature, and/or the like.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An antenna system comprising:
 a transmission member; and
 an antenna at a distal end of the transmission member, the antenna including a first conductive arm, an insulator extending around the first conductive arm, and a second conductive arm wound around at least a first portion of the insulator to form a second conductive arm coil, wherein a property of the insulator varies along an insulator longitudinal axis, and wherein the insulator includes a set of formed patterns along at least a portion of the insulator longitudinal axis.

2. The antenna system of claim 1 wherein the property of the insulator that varies along the insulator longitudinal axis is an outer profile of the insulator.

3. The antenna system of claim 2, wherein the outer profile of the insulator is tapered from an insulator proximal end to an insulator distal portion.

4. The antenna system of claim 1, wherein the set of formed patterns vary along the insulator longitudinal axis.

5. The antenna system of claim wherein the set of formed patterns includes at least one of laser-cut slots extending through at least a second portion of the insulator, H-pattern cuts extending through at least a third portion of the insulator, or curved pattern slots.

6. The antenna system of claim 1, wherein the set of formed patterns includes at least one groove formed in the insulator.

7. The antenna system of claim 6, wherein the at least one groove is shaped to receive the second conductive arm coil.

8. The antenna system of claim 7, wherein the insulator includes a plurality of retention features extending from the insulator to maintain the second conductive arm coil within the at least one groove.

9. The antenna system of claim 7, wherein the antenna further includes:
an outer jacket extending around at least a portion of the second conductive arm and the at least a portion of the insulator; and
an adhesive material adapted to flow within the at least one groove to form a bond between the outer jacket and the insulator.

10. An antenna system comprising:
a transmission member; and
an antenna at a distal end of the transmission member, the antenna including a first conductive arm, an insulator extending around the first conductive arm, and a second conductive arm wound around at least a first portion of the insulator to form a second conductive arm coil, wherein a property of the insulator varies along an insulator longitudinal axis, wherein the insulator includes a first section comprised of a first material and a second section comprised of a second material, and wherein the first section and the second section are positioned at different locations along the insulator longitudinal axis.

11. The antenna system of claim 10, wherein the insulator further includes a third section comprised of a blend of the first material and the second material, and wherein the third section is positioned between the first section and the second section.

12. An antenna system comprising:
a transmission member; and
an antenna at a distal end of the transmission member, the antenna including
a first conductive arm,
an insulator extending around the first conductive arm, and
a second conductive arm wound around at least a portion of the insulator, the second conductive arm forming a second conductive arm coil extending across a transition between the transmission member and the insulator or between the insulator and a distal tip member coupled to a distal end of the insulator, wherein a property of the second conductive arm coil is different at the transition than at the portion of the insulator.

13. The antenna system of claim 12, wherein the property of the second conductive arm coil that is different at the transition than at the portion of the insulator is a pitch of the second conductive arm coil.

14. The antenna system of claim 13, wherein the transition is formed where the distal tip member is coupled to a distal section the distal end of the insulator.

15. The antenna system of claim 14, wherein the pitch of the second conductive arm coil is smaller at the transition than at the portion of the insulator.

16. The antenna system of claim 13, wherein the transition is formed where a distal section of the transmission member meets a proximal end of the insulator, and wherein the pitch of the second conductive arm coil is smaller at the transition than at the portion of the insulator.

17. The antenna system of claim 13, wherein the pitch of the second conductive arm coil is at least one of linearly varying, non-linearly varying, logarithmically varying, and varying according to a step function.

18. The antenna system of claim 12, wherein the property of the second conductive arm coil that is different at the transition than at the portion of the insulator is at least one of a cross section of a wire forming the second conductive arm coil or a material property of the second conductive arm coil.

19. The antenna system of claim 12, wherein an outer profile of the insulator varies along an insulator longitudinal axis of the insulator and wherein the property of the second conductive arm coil that is different at the transition than at the portion of the insulator is a diameter of the second conductive arm coil, the diameter corresponding with the outer profile of the insulator.

20. The antenna system of claim 12, wherein the transition is between the transmission member and the insulator.

* * * * *

UNITED STATES PATENT AND TRADEMARK OFFICE
CERTIFICATE OF CORRECTION

| | | |
|---|---|---|
| PATENT NO. | : 11,637,378 B2 | Page 1 of 1 |
| APPLICATION NO. | : 16/670847 | |
| DATED | : April 25, 2023 | |
| INVENTOR(S) | : Serena H. Wong | |

It is certified that error appears in the above-identified patent and that said Letters Patent is hereby corrected as shown below:

In the Specification

Column 5, Line 34, change "belp" to -- help --

In the Claims

Column 18, Line 23, in Claim 14, delete "a distal"

Column 18, Line 24, in Claim 14, delete "section"

Signed and Sealed this
Thirteenth Day of June, 2023

*Katherine Kelly Vidal*

Katherine Kelly Vidal
*Director of the United States Patent and Trademark Office*